United States Patent [19]
Cardoso et al.

[11] Patent Number: 5,899,232
[45] Date of Patent: May 4, 1999

[54] DEBRIS-RESISTANT HYDROPNEUMATIC VALVE

[75] Inventors: Louis Cardoso, Miami; Robert Autrey, Pembroke Pines, both of Fla.

[73] Assignee: Coulter International Corp., Miami, Fla.

[21] Appl. No.: 09/059,987

[22] Filed: Apr. 14, 1998

[51] Int. Cl.[6] ............................................. F16K 11/048
[52] U.S. Cl. ..................... 137/625.5; 251/118; 251/318
[58] Field of Search .................. 137/625.5; 251/118, 251/318

[56] References Cited

U.S. PATENT DOCUMENTS

| | | |
|---|---|---|
| 3,180,360 | 4/1965 | Pavlin .................................. 137/625.5 |
| 4,026,325 | 5/1977 | Loveless . |
| 4,520,369 | 5/1985 | Shackleton ........................ 137/625.5 X |
| 5,067,521 | 11/1991 | Jeubs et al. ............................ 137/625.5 |
| 5,190,076 | 3/1993 | Kloehn . |

*Primary Examiner*—John Fox
*Attorney, Agent, or Firm*—Warren W. Kurz

[57] ABSTRACT

A poppet valve apparatus is structured to reduce the rate of build-up of fluid-borne debris within its internal architecture. The inlet and outlet ports are arranged tangential to the internal cylindrical walls defining the valve's flow chambers, whereby a circular flow pattern is produced within the valve interior, and a specially contoured flow director efficiently redirects the circular flow pattern through a circular annulus defined by a valve seat and a sealing ring.

6 Claims, 5 Drawing Sheets

DEBRIS-RESISTANT HYDROPNEUMATIC VALVE

BACKGROUND OF THE INVENTION

1. Field of the Invention

This invention relates to the field of fluid handling and, more particularly, to improvements in so-called "poppet valves" for controlling the flow of a pressurized fluid. More specifically, the invention relates to a poppet valve that is structured to reduce the rate at which debris associated with the fluid flowing through the valve accumulates within the valve's internal architecture and thereby degrades the valve performance.

2. Discussion of the Prior Art

In various medical instruments used to analyze blood and other body fluids, fast-acting "poppet" valves are commonly used to control the flow of small volumes of fluids, such as blood, saline and reagent solutions, between the various work stations of the instrument. In general, such valves comprise an inlet port through which a fluid is presentable to a flow chamber, one or more outlet ports operatively connected to the flow chamber for directing fluid away from the valve, and one or more valving mechanisms for selectively enabling or preventing fluid flow between the valve's flow chamber and it outlet port(s). Typically, each of the valving mechanisms includes a valve seat formed in a wall of the flow chamber, such seat providing an opening through which fluid can escape the confines of the flow chamber, and a movable valving member for quickly opening and closing the valve seat to thereby change the ON/OFF state of the valve. Poppet valves having only one valve seat and two ports (i.e., inlet and outlet ports) are referred to as "two-way" valves, and those having two valve seats and three ports (i.e., one inlet port and two outlet ports) are commonly referred to as "three-way" valves. In a three-way valve construction, fluid enters the inlet port, and is selectively expelled through either one of two outlet ports. Specifically, the particular outlet port through which fluid is expelled is determined by the position of the movable valving member which functions to obstruct fluid flow through one outlet port, while simultaneously permitting fluid flow through the other port. Of course, this state can be reversed by moving the movable valving member to an opposing position. Typically, the positioning of the valving member is accomplished through associated solenoid, pneumatic, or other similarly effective means.

An example of a conventional three-way poppet valve is disclosed by Kloehn in U.S. Pat. No. 5,190,076. As is common of many poppet valves, the Kloehn valve is operated by an axially-movable valve stem which, upon being moved, acts to deflect a pair of flexible diaphragms so as to position them to either permit or obstruct the passage of fluid through one of two valve seats which they respectively overly. Depending on the axial position of the valve stem, one of the diaphragms will be urged against one valve seat so as to effectively obstruct fluid flow therethrough, while the other diaphragm will be slightly separated from the other valve seat so as to enable fluid to be expelled through its associated outlet port.

Another type of poppet valve is that disclosed by Loveless in U.S. Pat. No. 4,026,325. The internal architecture of the Loveless valve differs from that of the Kloehn valve in that fluid flow is controlled by a resilient seal ring secured about the periphery of a plunger that is supported by the valve stem. As the valve stem moves axially, the plunger, and its associated resilient seal ring, moves between a valve-closing position in which the seal ring is pressed against the valve seat so as to obstruct fluid flow, and a valve-opening position in which the seal ring is separated from the valve seat so to enable fluid to pass through the valve seat and exit through an outlet port.

While the above-mentioned valve designs may operate effectively when used to control the flow of purified liquids, both encounter a problem when transmitting fluids containing a significant amount of debris or other material that may come out of a suspension or solution and stick to the mating surfaces of valving elements. In the case of blood, such debris is in the form of protein, lipids, and cell fragments found in the serum, all of which are adhesive in nature and tend to stick on any surface they encounter. In the Kloehn valve, such debris will accumulate on the planar surfaces of the diaphragms and the valve seat, causing a decline in the sealing effect of these mating elements. Similarly, the Loveless valve will experience debris build-up on the sealing ring and valve seats, causing fluid to leak to pass the ring seal prematurely. In both valves, debris build-up is hastened as a result of the particular method employed to introduce fluid into the interior of the valve. In particular, in both the Kloehn and the Loveless valves, fluid is introduced into the valve interior such that a highly turbulent flow pattern is produced, with much of the fluid making "head-on" (i.e., steep angle) contact with the surfaces of the various valving elements, such as the plunger or valve stem, seal ring, or the valve seat; as a result, some of the adhesive debris or particulate matter present in the fluid will attach itself to the surfaces encountered and accumulate thereon. After a period of continued use, accumulation of debris will reach a level where the valve fails to either effectively prevent fluid flow, or enable fluid flow at a desired flow rate. Thus, it would be desirable to provide a valving apparatus of the above type in which the rate at which debris accumulates on the internal mating surfaces is significantly reduced, whereby the mean-time-between-failure is significantly increased.

SUMMARY OF THE INVENTION

In view of the foregoing, an object of the present invention is to provide a poppet valve that delays the build up of debris within its internal architecture and thereby prevents premature leakage, reduced flow or failure.

As suggested above, the invention contemplates an improved poppet valve architecture which is particularly adapted to slow down the rate at which fluid-borne debris is deposited on the mating, fluid-sealing surfaces of the valve, whereby the anticipated lifetime of the valve is dramatically increased. Like the poppet valves of the prior art, the poppet valve of the invention comprises (a) a housing having an endless inner wall which defines a cylindrically-shaped flow chamber for receiving fluid from an external source, such chamber having a conical-shaped valve seat located at one end thereof through which fluid within the flow chamber may exit therefrom; and (b) a movable valving member which is selectively movable between a first position in which it operates to seal the valve seat and thereby prevent fluid flow from the flow chamber, and a second position spaced from the valve seat, thereby enabling fluid flow from the chamber. Unlike the prior art devices, however, the poppet valve of the invention is characterized by (a) a specially contoured (preferably having a parabolic or hyperbolic shape) flow deflector, concentrically arranged within the cylindrical flow chamber on the longitudinal axis thereof, and (b) means for introducing fluid into the flow chamber from a direction substantially tangent to the cylindrical wall thereof. The advantageous technical effect of this combination of elements is that fluid entering the flow chamber is caused to rotate and swirl about the longitudinal axis of the flow chamber at high velocity while being smoothly deflected by the flow deflector toward a direction which is approximately parallel to the conical surface of the valve seat. When the valve seat is unobstructed by the valving member, the rotational movement of the fluid tends to cause the fluid to impinge upon the valve seat and valving element at low angles, thereby reducing any tendency for debris in the fluid to stick to the valve surfaces. This tendency to avoid sticking is further enhanced by the speed at which the fluid is caused to flow through the valve seat.

Preferably, the valving member is in the form of a resilient sealing ring which is supported on an axially movable valve stem. Also preferred is that the conical valve seat has a compound surface defined by first and second conical walls, one wall being at a steeper angle relative to the chamber's longitudinal axis than the other. As better explained below, as the sealing ring enters the valve seat and initially engages the conical surface of shallower angle, it tends to push any accumulated toward the steeper surface where it is less likely to stick.

Thus, the invention contemplates two distinct valve cleansing aspects: (1) the continuous centrifugal cleaning action of the seat by the rotational fluid flow in the flow chamber; and (2) the pushing of particles and debris away from the valve seat by the sealing ring and the resulting velocity increase as the fluid exits the flow chamber.

The invention will be better understood from the ensuing detailed description of preferred embodiments, reference being made to the accompanying drawings.

DETAILED DESCRIPTION OF PREFERRED EMBODIMENTS

Figure 1:
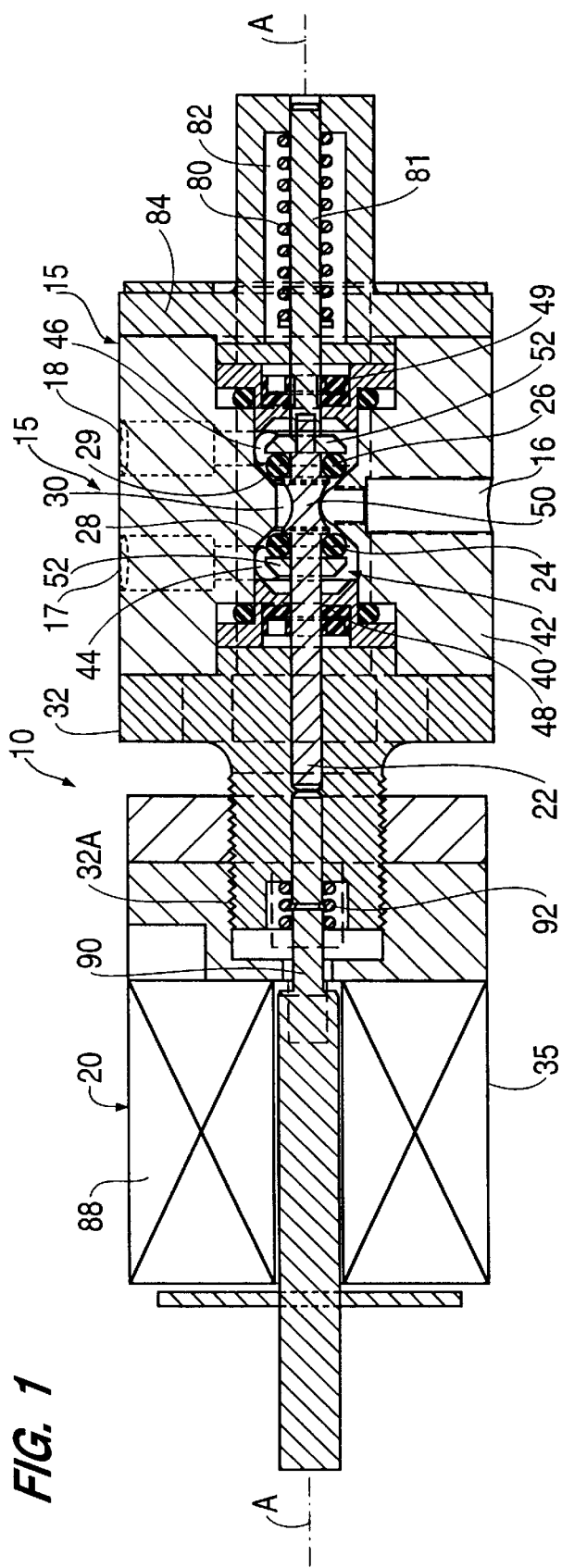
FIG. 1 is a cross-sectional view of a three-way poppet valve assembly embodying the present invention.

Referring to the drawings, there is illustrated in FIG. 1 a three-way poppet valve apparatus 10 which is structured in accordance with a preferred embodiment of the invention. Such apparatus includes a valving portion 15 which is selectively actuable to control the flow of a liquid between an entrance port 16 and either of two outlet ports 17, 18, and a valve-actuating portion 20. As explained below, the valve-actuating portion operates to control the position of a valve stem 22 which supports a pair of resilient sealing rings 24,26 used to selectively open and close a pair of valve seats 28 and 29 disposed at opposite ends of a flow chamber 30 which receives liquid from an external source via inlet port 16. Actuating portion 20 is attached to valve portion 15 by an end cap 32 having a threaded extension 32A. Preferably, actuating portion 20 comprises an electrical solenoid 35 or the like which operates, as described below, to control the axial position of the valve stem 22, i.e., along longitudinal axis A, and the sealing position of the sealing rings 24,26 relative to their associated valve seats 28,29, respectively.

Figure 2:
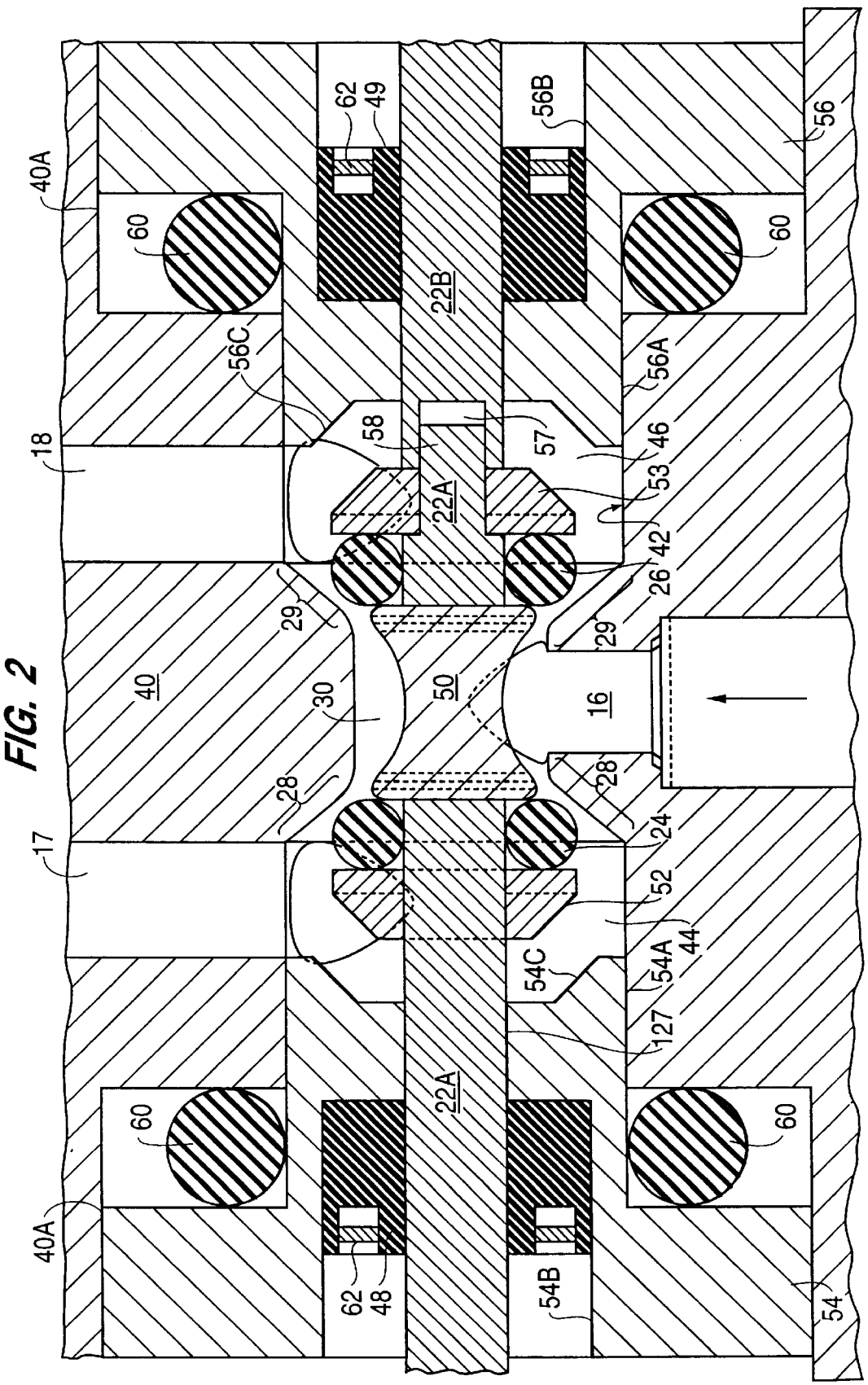
FIG. 2 is an enlarged cross-sectional view of the fluid flow-controlling portion of the FIG. 1 valve assembly.
Figure 3:
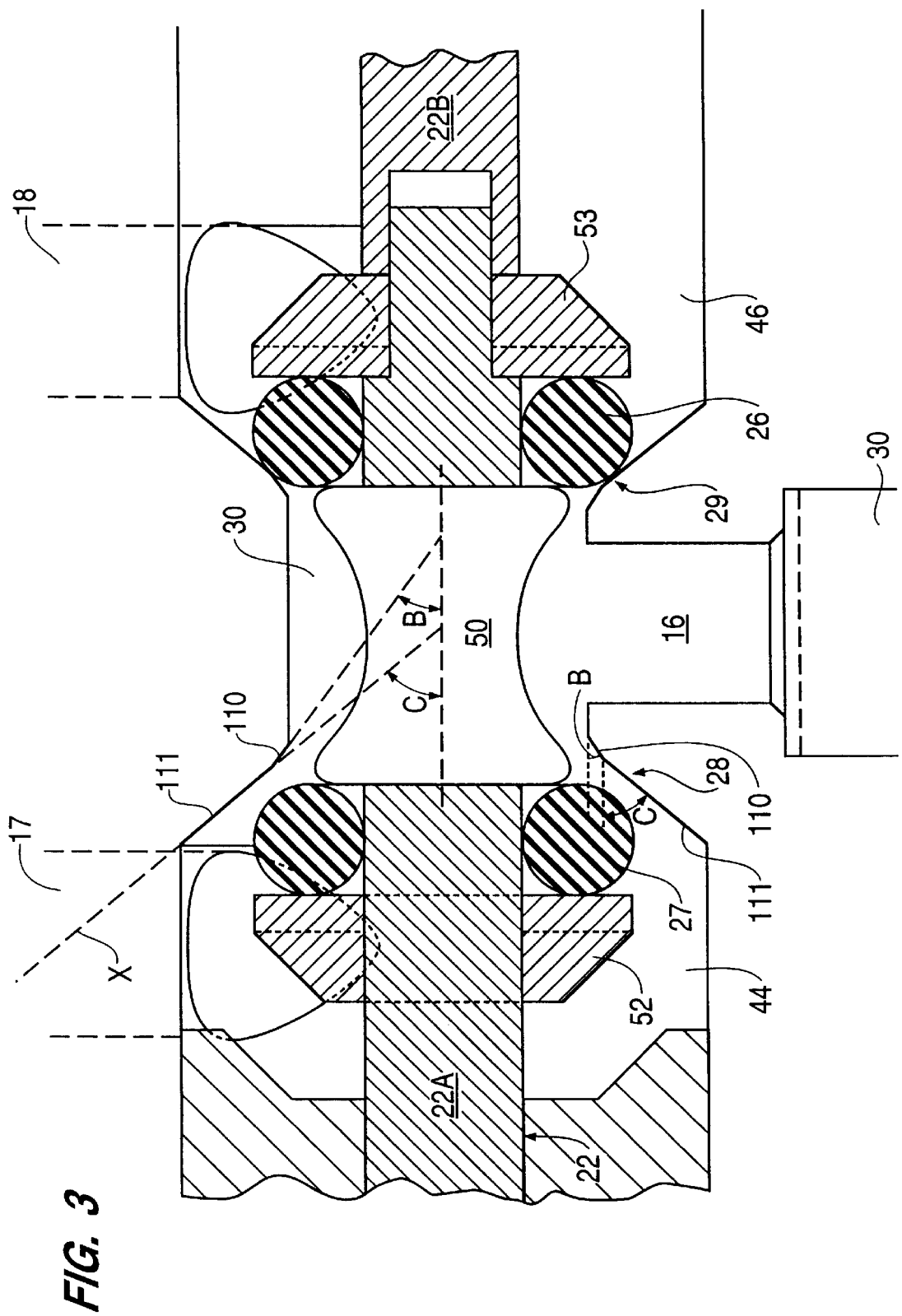
FIG. 3 is a further enlarged cross-sectional view of the flow chamber and valve seats of the FIG. 1 apparatus.

Referring additionally to FIGS. 2 and 3, the valving portion of the poppet valve apparatus of the invention preferably comprises a substantially cylindrical central housing 40 having a central opening 42 of circular transverse cross-section extending axially throughout its interior for receiving the valve stem and its associated valving elements. The diameter of opening 42 varies along its length to define (i) the aforementioned flow chamber 30, (ii) first and second exit chambers 44 and 46, and (iii) the conically-shaped valve seats 28 and 29. Preferably, housing 40 is constructed of polyetherketoneketone (PEEK) or other similar material so as to keep wear and erosion of the internal architecture to a minimum. Valve stem 22 is supported for sliding movement within opening 42 by a pair of sealing bushings 48, 49. In the vicinity of its midpoint, the valve stem supports, or has integrally formed therewith, a parabolically-shaped flow director 50 and the aforementioned sealing rings 24, 26, which are preferably made of rubber or the like. Each of the sealing rings is arranged and fixed in place on the valve stem between an end of the flow director 50 and one of two seal retainers 52,53 supported by the valve stem. The sealing rings are spaced apart such that, as the valve stem moves to the left, as viewed in the drawings, sealing ring 26 seals the valve seat 29 and prevents fluid flow therethrough. During the same movement, sealing ring 24 becomes spaced from the valve seat 28, thereby enabling fluid flow therethrough. Thus, during normal operation of the valve, fluid will typically enter the valving apparatus through port 16. This incoming fluid will flow through flow chamber 30, pass through one or the other valve seats 28,29 to either of chambers 44 or 46, and exit through either of the ports 18 or 17.

In order to ensure that fluid does not leak out of the chambers 44 and 46, a pair of circular plate members 54,56 are slidably mounted on the valve stem 22. Note, as shown in the enlarged view of FIG. 2, the valve stem is actually formed by two separate portions 22A and 22B to facilitate assembly. Portion 22A supports the flow director 50, both sealing rings 24 and 26, and seal retainer 52. Valve stem portion 22B supports the seal retainer 53 at its end and is provided with an axial opening 57 for receiving the reduced diameter end 58 of valve stem portion 22A. Each of the circular plate member 54, 56 fits within a suitably dimensioned circular recess 40A formed in each end of housing 40 and is provided with a shoulder portion 54A, 56A, respectively, for supporting a sealing ring 60. The sealing rings 60 prevent the escape of fluid between the plate members and valve housing 40. Each of the plate members 54, 56 is provided with a circular recess 54B, 56B, respectively, for receiving the aforementioned sealing bushings 48, 49. Each of the sealing bushings is provided with a recess for receiving a spring retainer 62 which exerts radial forces against the valve stem and plate members to prevent fluid flow along the valve stem. Preferably, the respective interior sides 54C, 56C of plate members 54, 56 are concave in shape so as to provide an efficient flow path for fluid rotating within exit chambers 44 and 46. Preferably, the outboard sealing bushings 62 are composed of a low friction material, such as ultrahigh molecular weight polyethylene (UHMWPE), to reduce breakaway, running friction, and wear from corrosive or particulate media.

As shown in FIG. 2, and more clearly in FIG. 3, valve seats 28 and 29 serve to connect flow chamber 30 to exit chambers 44 and 46, respectively. Both of the valve seats are identical in shape, and each preferably comprises a compound conical surface comprising a first conical wall 110 having a first half-cone angle B, and a second conical wall 111 having a second half-cone angle C which, as shown, is somewhat larger than half-cone angle B. As will be explained later, the value of the angle C of second conical wall 111, in combination with the particular shape of flow director 50, serves to improve fluid flow through the valve seat during operation of the valve. Furthermore, because angle C is larger than angle B, first conical wall 110 further prevents the build-up of debris along the valve seat by effectively increasing the area that must be filled by debris for there to be an associated clogging problem.

Figure 4B:
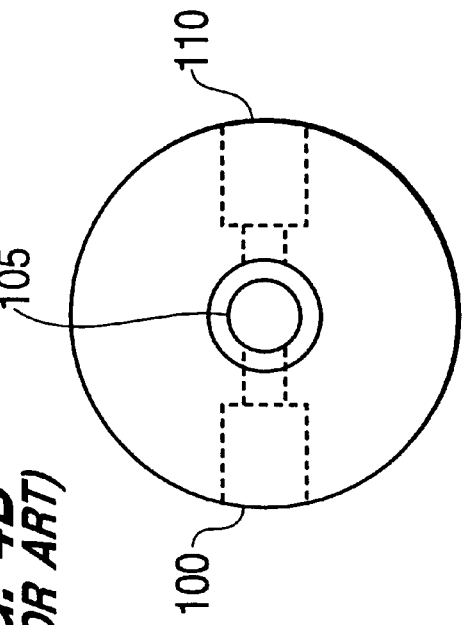
FIGS. 4A and 4B are end views comparing the valve shown in FIG. 1 with a similar valve of the prior art.
Figure 4A:
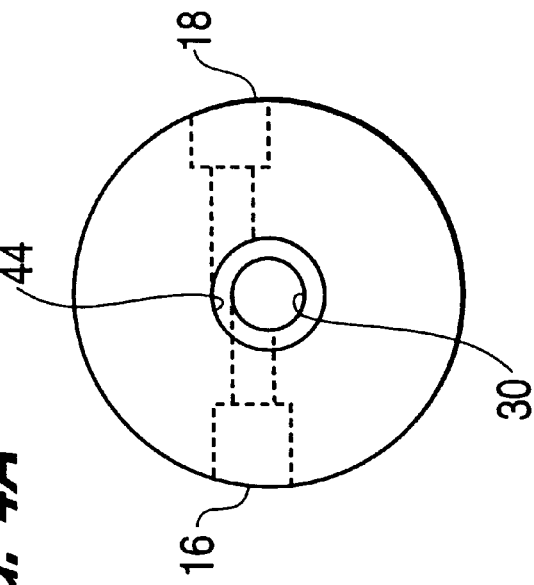

In order to achieve the debris-resistant characteristic of the present invention, inlet port 16 is positioned so as to tangentially connect with cylindrical wall of flow chamber 30, as shown in FIG. 4A. This particular connection causes incoming fluid to flow in a rotational manner, about axis A, which results in a centrifugal force that works to prevent the accumulation of debris along the interior architecture of the valving apparatus. Furthermore, the tangential connection allows the valve to exploit the incoming velocity of the fluid which further enhances the rate of rotational flow. In like manner, outlet port 18 and 17 are tangentially connected to the cylindrical wall of exit chamber 44 and 46, respectively, so that rotating fluid may efficiently exit the valve apparatus. In contrast, FIG. 4B shows an end view of a typical prior art valve where no consideration is given to the flow of fluid within the valve; indeed, a substantial volume of incoming fluid introduced by port 100 collides with valve stem 105 before eventually exiting through port 110. This collision has the effect of significantly reducing the velocity at which fluid flows within the interior of the valve; consequently, no particular flow results that reduces the amount of debris along the interior architecture. Note, in the valve of the invention, the incoming and rotating fluid will impinge the chamber walls, sealing rings and valve seats at low angles, thereby reducing any tendency for debris in the fluid to stick to the surfaces encountered.

As noted above, the flow director 50 is shaped to enhance the self-cleaning action of the valve. The shape of the flow director operates to direct the incoming fluid, which is entering the flow chamber from a direction substantially perpendicular to the valve axis A, toward the valve seats 28 and 29 and towards the annulus defined by the valve seat and its mating sealing ring. Thus, the surface of the flow director initially operates to redirect the incoming fluid in a direction 90 degrees relative to its direction of entry, and eventually directs the fluid to a direction substantially parallel to the conical valve seats. Preferably, the fluid-encountering surface of the flow director 50 is of a parabolic or hyperbolic shape, the extension X of which runs substantially parallel to the conical surface 111 of the valve seat so as to provide a conical channel for further enhancing the rotational fluid flow within flow chamber 25. As the incoming fluid rotates about flow director 50, the resulting centrifugal force will prevent particles and debris from settling or accumulating on the inner wall of the flow chamber, as well as on the mating surfaces of the valving elements. Moreover, the shape of the flow director 50 ensures a smooth and unobstructed flow of the fluid through the valve seats. Preferably, the half-cone angle B is about 30 degrees, and the half-cone angle C is about 60 degrees.

As is shown in FIG. 2, flow director 50 is only slightly longer length than the distance between the edges of the valve seats. This ensures that the sealing rings, located on opposite sides of flow director 50, are located in relatively close proximity to the valve seat. As a consequence, the small distance between the valve seat and the seal causes a mild flow restriction that results in increased fluid velocity of the rotational flow through the seat. This increased fluid velocity further enhances the cleaning action of the valve by effectively pushing debris away from the valve seat and seal in a direction perpendicular to the centrifugal force created by the rotating fluid. In effect, the higher velocity of the rotational flow through the valve seat, in conjunction with the centrifugal force associated with the rotational flow, acts to prevent particles or debris from settling on the valve seat.

In use, valve stem 22 is normally biased towards the left, as viewed in the drawings, whereby sealing ring 26 engages and seals shut the valve seat 29. Meanwhile, sealing ring 24 becomes spaced from valve seat 28 allowing fluid to flow therethrough. Thus, when fluid is applied to the inlet port 16, it will normally exit through port 17. Such biasing of the valve stem to the right is effected by a coil spring 80 which surrounds an extension 81 of the valve stem. Coil spring 80 is housed in a recess 84 formed in an end cap 86 attached to housing 40. The state of the valve is reversed, in which case valve seat 29 is open and valve seat 28 is closed, by energizing a solenoid coil 88. When energized, the solenoid drives its plunger 90 to the right, thereby overcoming the force of a spring 92 used to retain the plunger within the coil, and also overcoming the force of coil 80. As plunger 92 moves to the right, it abuts an end of the valve stem, driving the stem rightward until sealing ring 24 engages and seals valve seat 28, and sealing ring 26 becomes spaced from valve seat 29. Preferably, the solenoid windings and flux collectors are designed such that actuation forces are maximum for the needed stroke. It will be appreciated that push-pull type solenoids are the most suitable for the short actuation strokes found in this application.

Figure 5:
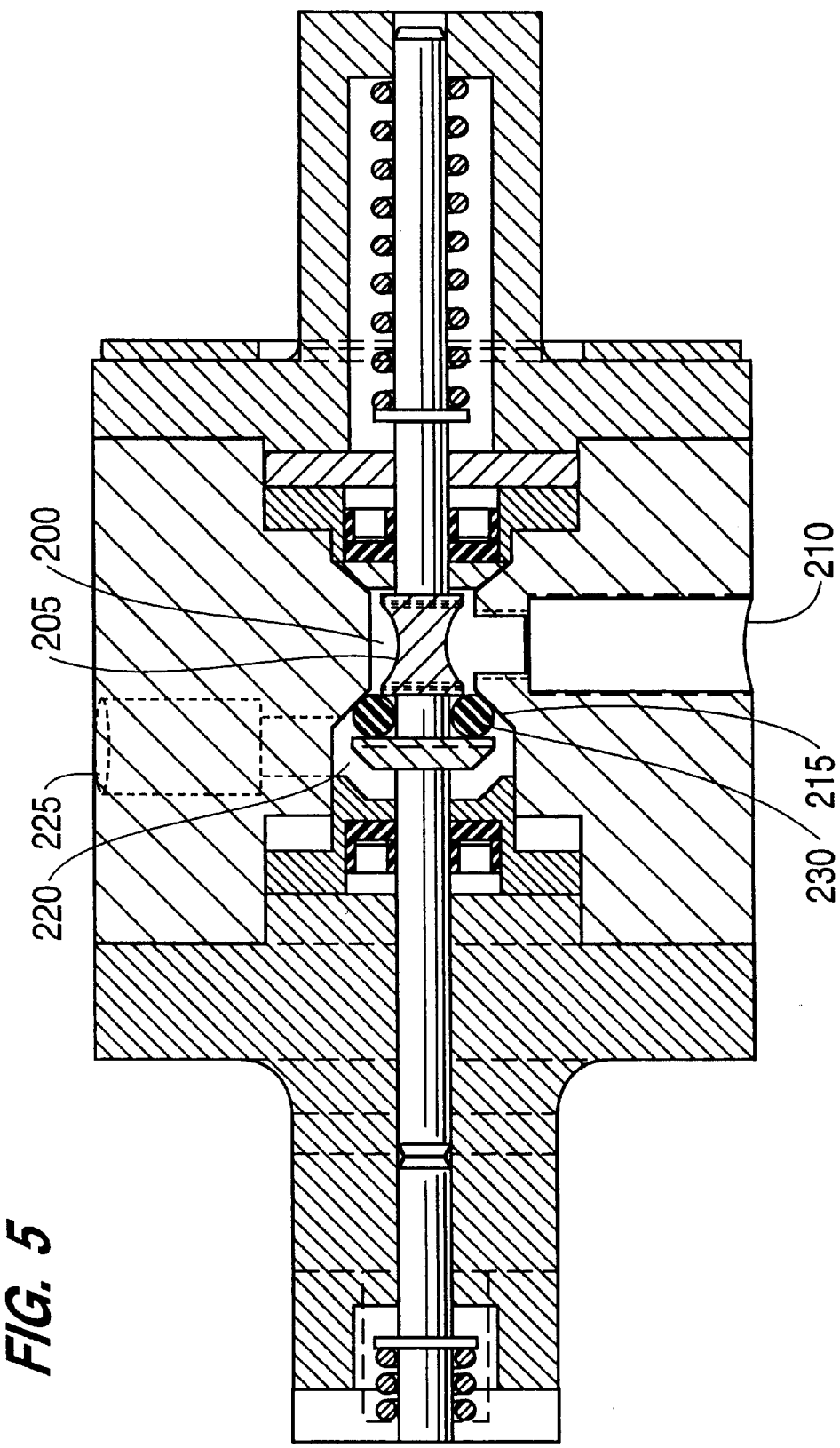
FIG. 5 is a cross-sectional illustrations of an alternative embodiments of the invention.

In the above detailed description, the invention is disclosed as a three-way valving apparatus; that is, the operator of the valve can selectively provide for the passage of fluid flow through one of two ports. However, as is shown in FIG. 5, it is possible to present a two-way valving apparatus embodying the invention. In this alternative embodiment, the operator can select between fluid flow or no fluid flow. As in the case of the three-way valve of FIG. 1, the two-way valve of FIG. 5 comprises a flow chamber 200, flow director 205 disposed within the flow chamber, inlet port 210 for introducing fluid to flow chamber 200 from an external source, and valve seat 215. Unlike the three-way valve, the two-way valve does not include a second chamber from which fluid is expelled through a second outlet port; rather, the two-way valve is limited to a single chamber 220 from which fluid is expelled through outlet port 225 during operation. Therefore, when the valve is actuated by actuation means (not shown), fluid flow will cease. Specifically, seal 230 will be urged against valve seat 220 and thereby obstruct rotational fluid flow through the valve seat.

The invention has been described with reference to certain preferred embodiments but it will be appreciated that variations and modifications can be effected without departing from the spirit of the invention. Such variations and modifications are intended to fall within the scope of the appended claims.

What is claimed is:

1. In a valving apparatus for controlling fluid flow, said apparatus comprising
 (a) a housing having an endless inner wall which defines a cylindrically-shaped flow chamber for receiving fluid from an external source, such chamber having a longitudinal axis and a conical-shaped valve seat defined by a conical surface located at one end thereof through which fluid within the flow chamber can exit therefrom; and (b) a movable valving member which is selectively movable between a sealing position in which it operates to seal the valve seat and thereby prevent fluid flow from the flow chamber, and a non-sealing position, spaced from the valve seat, in which it enables fluid flow from the chamber, the improvement comprising:

(a) means for introducing fluid into the flow chamber from a direction substantially tangent to the cylindrical wall thereof, whereby fluid entering the flow chamber tends to rotate about said longitudinal axis to produce a rotational flow pattern, and (b) a flow deflector, concentrically arranged within the cylindrical flow chamber on said longitudinal axis, for deflecting the rotational flow pattern in a direction substantially parallel to the conical surface of said valve seat.

2. The apparatus as defined by claim 1 wherein said flow deflector has a fluid-encountering surface having a parabolic or hyperbolic shape.

3. The apparatus as defined by claim 1 wherein said conical surface has first and second conical surface portions which are disposed at different angles relative to said longitudinal axis.

4. A three-way poppet valve comprising:

(a) a housing having an endless inner wall which defines a cylindrically-shaped flow chamber for receiving fluid from an external source, such chamber having a longitudinal axis and a pair of opposing conical-shaped valve seats, defined by respective conical shaped surfaces, through which fluid within the flow chamber can exit therefrom;

(b) an inlet port for introducing fluid into said flow chamber from a direction substantially tangent to said inner wall, whereby fluid entering the flow chamber tends to rotate about said longitudinal axis to produce a rotational flow pattern;

(c) a pair of movable valving members for selectively sealing and unsealing said valve seats; and (d) a flow deflector, concentrically arranged within the cylindrical flow chamber on said longitudinal axis for deflecting the rotational flow pattern in a direction substantially parallel to the conical surface of said valve seat.

5. The apparatus as defined by claim 4 wherein said flow deflector has a parabolic or hyperbolic shape.

6. The apparatus as defined by claim 4 wherein said conical surface has first and second conical surface portions which are disposed at different angles relative to said longitudinal axis.

* * * * *